United States Patent [19]

Azar

[11] Patent Number: 5,634,919

[45] Date of Patent: Jun. 3, 1997

[54] CORRECTION OF STRABISMUS BY LASER-SCULPTURING OF THE CORNEA

[75] Inventor: Dimitri T. Azar, Rockville, Md.

[73] Assignee: The Johns Hopkins University, Baltimore, Md.

[21] Appl. No.: 24,174

[22] Filed: Feb. 22, 1993

[51] Int. Cl.[6] .................................................. A61M 5/06
[52] U.S. Cl. ............................ 606/5; 606/3; 606/10; 606/13; 606/17
[58] Field of Search .......................... 606/2–6, 10–17; 219/121.6, 121.67–121.69, 121.72–121.75, 121.78–121.81, 121.85

[56] References Cited

U.S. PATENT DOCUMENTS

| | | | |
|---|---|---|---|
| 3,904,281 | 9/1975 | Jampolsky | 351/175 |
| 4,648,400 | 3/1987 | Schneider et al. | 606/5 |
| 4,718,418 | 1/1988 | L'Esperance, Jr. | 606/5 |
| 4,729,372 | 3/1988 | L'Esperance, Jr. | 606/5 |
| 4,798,204 | 1/1989 | L'Esperance, Jr. | 606/5 |
| 4,994,058 | 2/1991 | Raven et al. | 606/5 |
| 5,152,759 | 10/1992 | Parel et al. | 606/5 |
| 5,163,934 | 11/1992 | Munnerlyn | 606/3 |

FOREIGN PATENT DOCUMENTS 9111158  8/1991  WIPO .................................. 606/5

OTHER PUBLICATIONS

Photoablative Reprofiling of the cornea using an excimer laser: Photorefractive Keratectomy; Marshall et al; Lasers in Ophthalmology; vol. 1, No. 1, pp. 21–48 (1986).

*Primary Examiner*—David M. Shay
*Attorney, Agent, or Firm*—Banner & Witcoff, Ltd.

[57] ABSTRACT

The present invention consists of methods and apparatus for laser ablation of the cornea to correct strabismus. The laser beam is controlled by a system of limiting shutters to cut prism lenses into the cornea. The ablation is to remain substantially within the Bowman's layer, keeping scarring to a minimum.

11 Claims, 16 Drawing Sheets

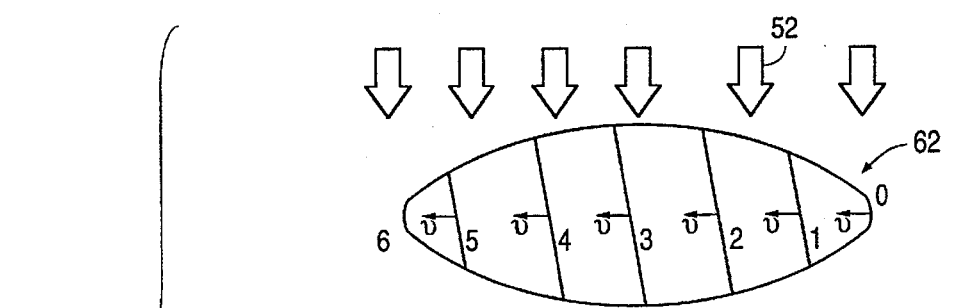
FIG. 6A
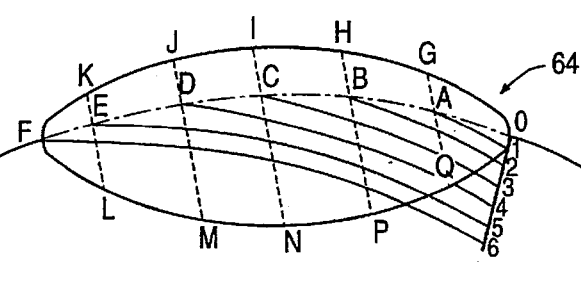
FIG. 6B
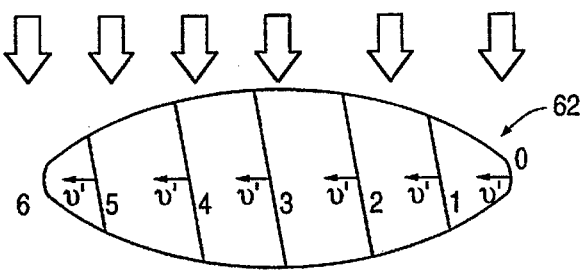
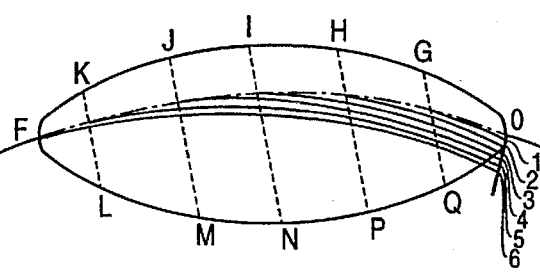

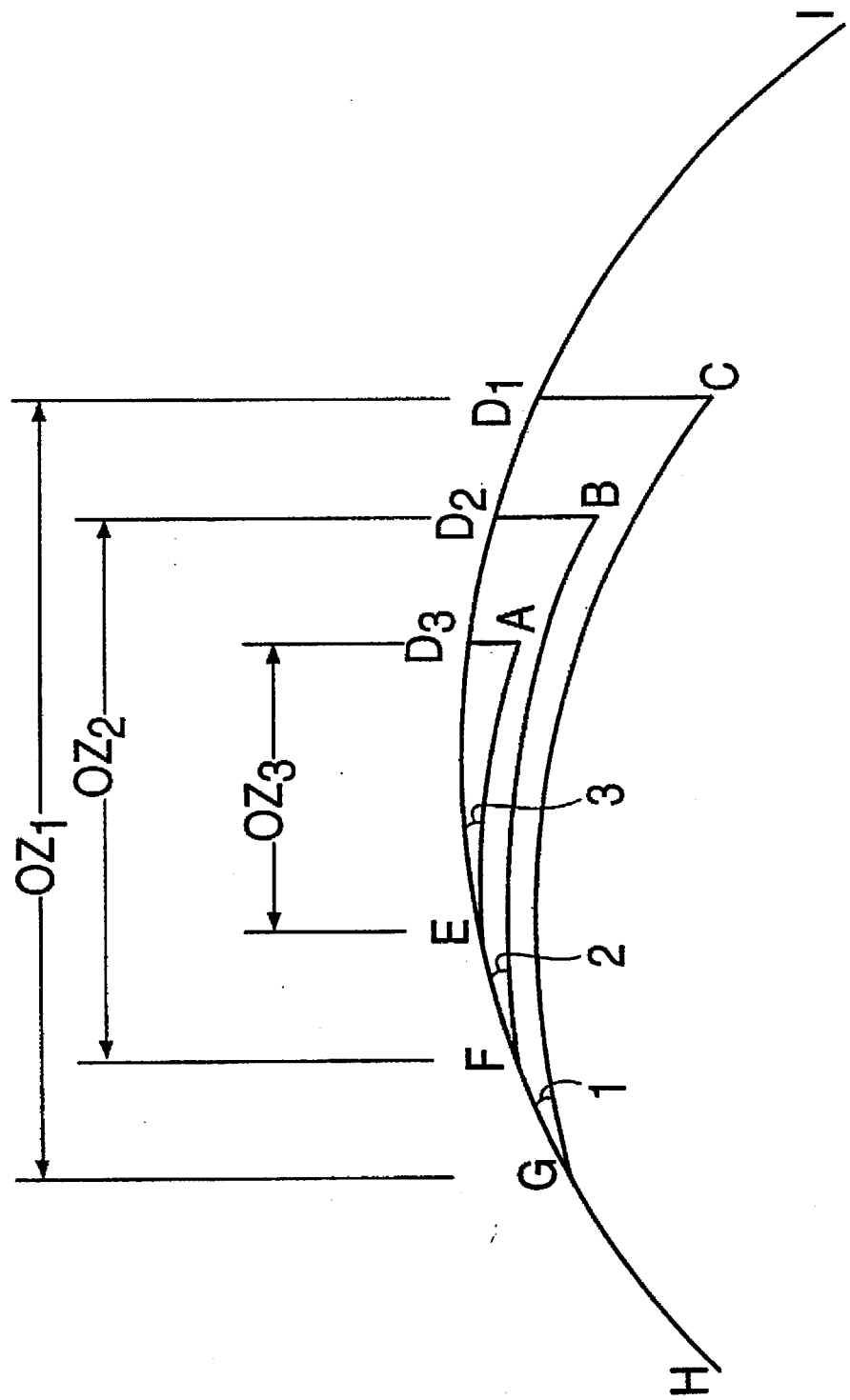

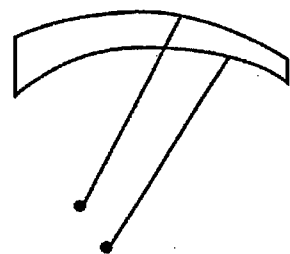
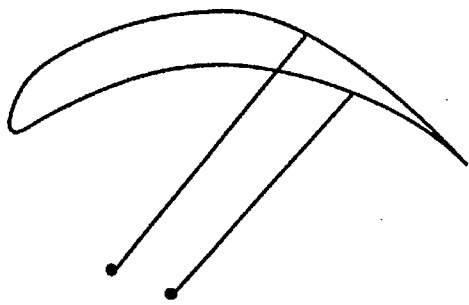

CORRECTION OF STRABISMUS BY LASER-SCULPTURING OF THE CORNEA

BACKGROUND OF THE INVENTION

1. Field of the Invention

The present invention relates to a method and apparatus for ablation of the cornea with a laser and in particular relates to sculpturing prism lens into the cornea to correct strabismus (non-alignment of the optical axes).

2. Description of the Prior Art

It is known in the art to use an excimer laser to sculpture the human cornea in order to correct a refractive error. U.S. Pat. No. 4,665,913 entitled "Method for Ophthalmological Surgery" invented by Francis L'Esperance teaches ablative photo decomposition to change the front surface of the cornea from greater to a lesser spherical curvature or from a lesser to greater spherical curvature. This procedure change the refractive error thus effecting reduction in a myopic or in a hyperopic condition. U.S. Pat. No. 4,798,204 also issued to L'Esperance teaches a technique of sculpturing the epithelium-free Bowman's membrane of the cornea to achieve a corrected-curvature profile.

The prior art does not teach how to correct strabismus (non-alignment of the optical axes) by laser sculpturing. Only changes in curvature effecting refractive error is taught. The prior art does not teach shaping a prism lens on the cornea.

SUMMARY OF THE INVENTION

Patients with strabismus (non-alignment of the optical axes) have eyes with visual axes that fail to meet at the objective point; this may produce a double image and results in diplopia (double vision when looking at near and distant objects). Poor vision may develop in children due to amblyopia (suppression of image formed on extra-foveal location in strabismus). In addition to being a birth defect, strabismus can occur following extraocular nerve paresis or ocular surgery. Quite frequently a patient will develop strabismus after cataract and ocular other surgery. This results in disturbing diplopia (double vision).

Current techniques used to deal with strabismus include fitting the patient with prism spectacles or surgically changing the length of one or more of the ocular muscles. Prismatic spectacles may be disfiguring and can result in optical aberrations. Generally surgery to change the length or insertion of the eye muscles can effect gross changes but rarely corrects the exact full degree of strabismus. It usually leaves the patient with some degree of lingering strabismus and diplopia due to over- or under-correction.

The present invention is a method and apparatus for very accurately sculpturing the cornea to correct strabismus. This technique can be used to correct the residual strabismus after muscle surgery, to supplement eye muscle surgery, to correct diplopia, or in many instances, could be the primary treatment of choice. Techniques encompassed by the present invention can make very slight prism diopter changes (in the order of 1 to 5 prism diopters) and/or greater degrees of prism diopter change in excess of 10 prism diopters (such as by sculpting Fresnel prisms).

The present invention teaches method and apparatus for sculpturing prism lens on the cornea. In a first embodiment a laser sculptured truncation procedure is used. In this technique a single prism lens in sculptured into the optical zone of the cornea. For small degrees of intended prismatic correction, the prism is sculptured into the thin Bowman's layer for optimal healing, but may extend deeper into stroma when necessary. This embodiment is most useful in cases of minimal prismatic correction and is particularly applicable for post-cataract vertical and horizontal diplopia.

A second embodiment uses a laser to sculpture a fresnel prism into the cornea. This method works particularly well when large prism diopter changes are necessary that require deeper ablations. For a given diopter change the fresnel prisms result in reduced depth of ablation than with the truncation embodiment. For intermediate degrees of intended prismatic corrections, the novel fresnel prisms are sculptured mostly into the Bowman's layer of the cornea and little post operative scarring will result. (The Bowman's layer, as will be discussed later, is acellular and reshaping will not result in scaring. Sculpturing of cellular portions of the cornea can result in transient scarring, which manifests itself as stromal haze and visual blurring obviously undesirable complications.)

The third embodiment of the present invention involves decentration of the cornea through laser sculpturing. Decentration involves either sculpturing the shape of the cornea to move the optical center from the visual axis or using spherical or Fresnel lens (not prism) to achieve configuration decentration of the optical axis of the cornea.

A fourth embodiment of the present invention involves using any of the above three embodiments in combination with spherical or astigmatic correction of associated refractive errors that are commonly present in conjunction with strabismic deviation. This is most commonly required in cases of pediatric strabismus where hyperopic or other spheroeylindrical spectacle corrections are needed in addition to extraocular muscle surgery.

A fifth embodiment of the present invention involves placing an ablatable prism over the cornea to sculpture the required prismatic correction on the corneal stroma. Fresnel or non-Fresnel ablatable prisms may be used. This method may employ modifications of the ablation to induce a combination of prismatic and spherocylindical corrections.

BRIEF DESCRIPTION OF THE DRAWINGS

FIG. 6A. Shows the result of the truncation method of prismatic corneal ablation at a slow shutter speed.

FIG. 6B. Shows the result of the truncation method of prismatic corneal ablation at a fast shutter speed.

FIG. 7. Shows the result of the truncation method of prismatic corneal ablation using various optical zones.

FIG. 15A. Shows the cross section of a minus lens ablatable element that can correct myopia.

FIG. 15B. Shows that by truncating the lens in FIG. 15A using laser ablation a new lens can correct diplopia (or strabismus) as well as myopia.

FIG. 15C. Shows the cross section of a plus lens ablatable element that can correct hyperopia.

FIG. 15D. Shows that by truncating the lens in FIG. C using laser ablation a new lens can correct diplopia (or strabismus) as well as hyperopia.

DETAILED DESCRIPTION OF THE PREFERRED EMBODIMENTS

Figure 1:
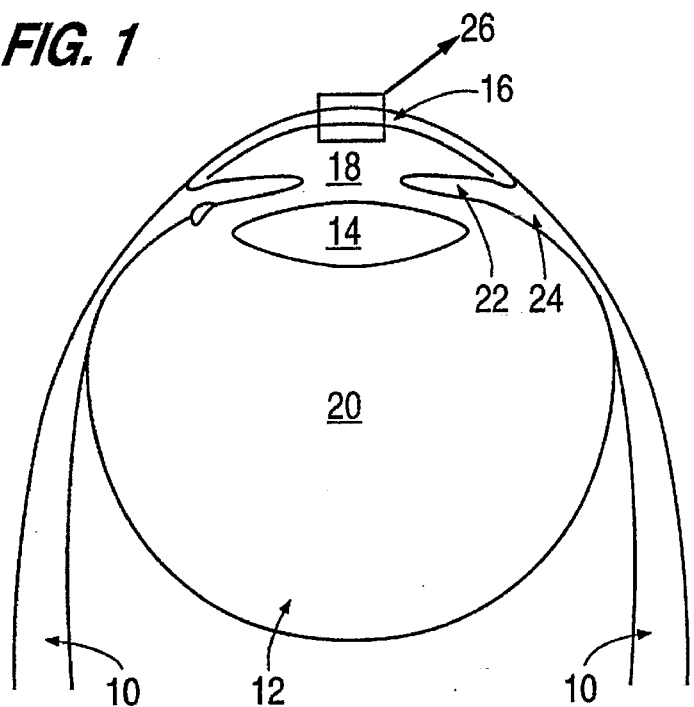
FIG. 1. An anatomical view of an eye comprising the major parts of the eye.
Figure 2:
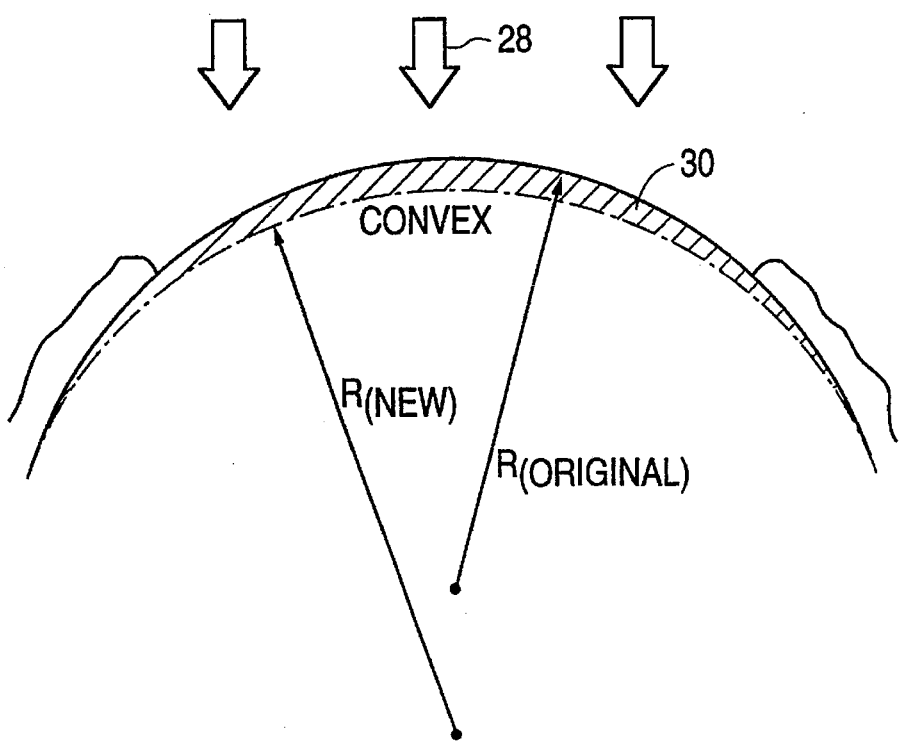
FIG. 2. A magnified view of block 26 of FIG. 1, showing the area to be sculptured by the laser.

In order to better understand this invention, discussion of the eye structure and the prior art ablation techniques is in order. FIG. 1 is an anatomical drawing of one eye showing: extraocular muscles 10, retina 12, lens 14, cornea 16, anterior chamber 18, vitreous 20, iris 22, ciliary body 24. The area of the cornea 16 in the optical zone is to be sculptured by a laser. The optical zone is the area of the cornea above the pupil (the pupil is the empty circle inside the iris 22). The block shown in FIG. 1 (labeled element 26) is a representative area of the cornea that is sculptured by the laser. The area in this block is expanded in FIG. 2 to show the prior art laser ablation technique to correct refractive errors. An excimer laser beam 28 is applied to the surface of the cornea and sculptures the curvature of the cornea. The radius of curvature is changed from R (original) to R (new) by ablation photo decomposition of the shaded portion of the cornea. This change of radius of curvature changes the refractive power of the cornea.

Figure 3:
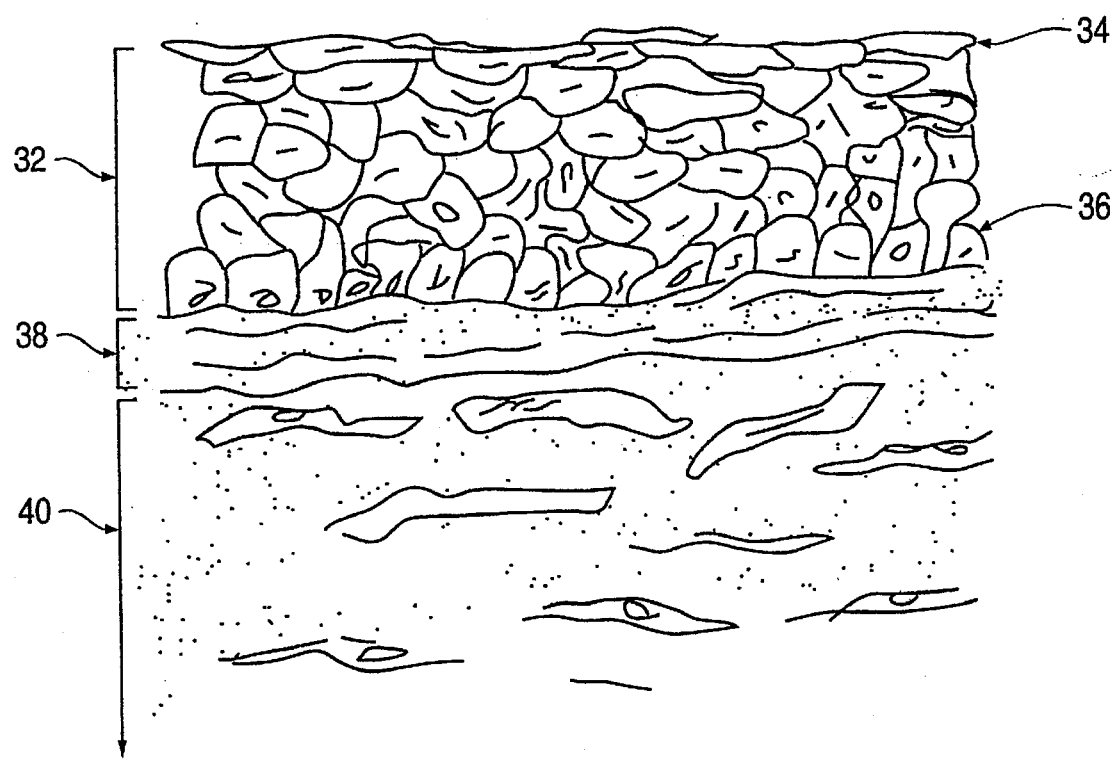
FIG. 3. A view of the anterior layers of an untreated human cornea.

FIG. 3 shown the anterior layers of the untreated human cornea. The outer epithelium layer 32 is approximately 40 um in depth and consists of a 5 to 7 layers of cells. The epithelium layer is made of superficial epithelial cells 34, one layer of basal epithelial cells 36, and intermediate cells located between these 2 cell layers. The Bowman's layer 38 is located beneath the epithelium and is a 12–15 um thick, an acellular layer consisting of collagen. The anterior stroma 40 is cellular, and is located below the Bowman's layer. In laser ablation procedures, the epithelium layer 32 is either mechanically removed or ablated with the laser; and the laser energy ablates the Bowman's layer 38 and a significant portion of the anterior stroma 40. After surgery, the outer epithelium layer will grow back. Ablation of the acellular Bowman's layer is known to results in no scaring. However, ablation of the lower anterior stroma 40 is known to cause scarring due to activation of the stromal cells which will result in scarring. This, at times, may cause the patient to see a hazy image. Laser ablation techniques that are essentially restricted to sculpturing the 12–15 um Bowman's layer with little or no ablation of the underlying anterior stroma may reduce the scarring. Many of the inventive techniques described later in this specification attempts to maximize ablations limited to the Bowman's layer.

Figure 4A:
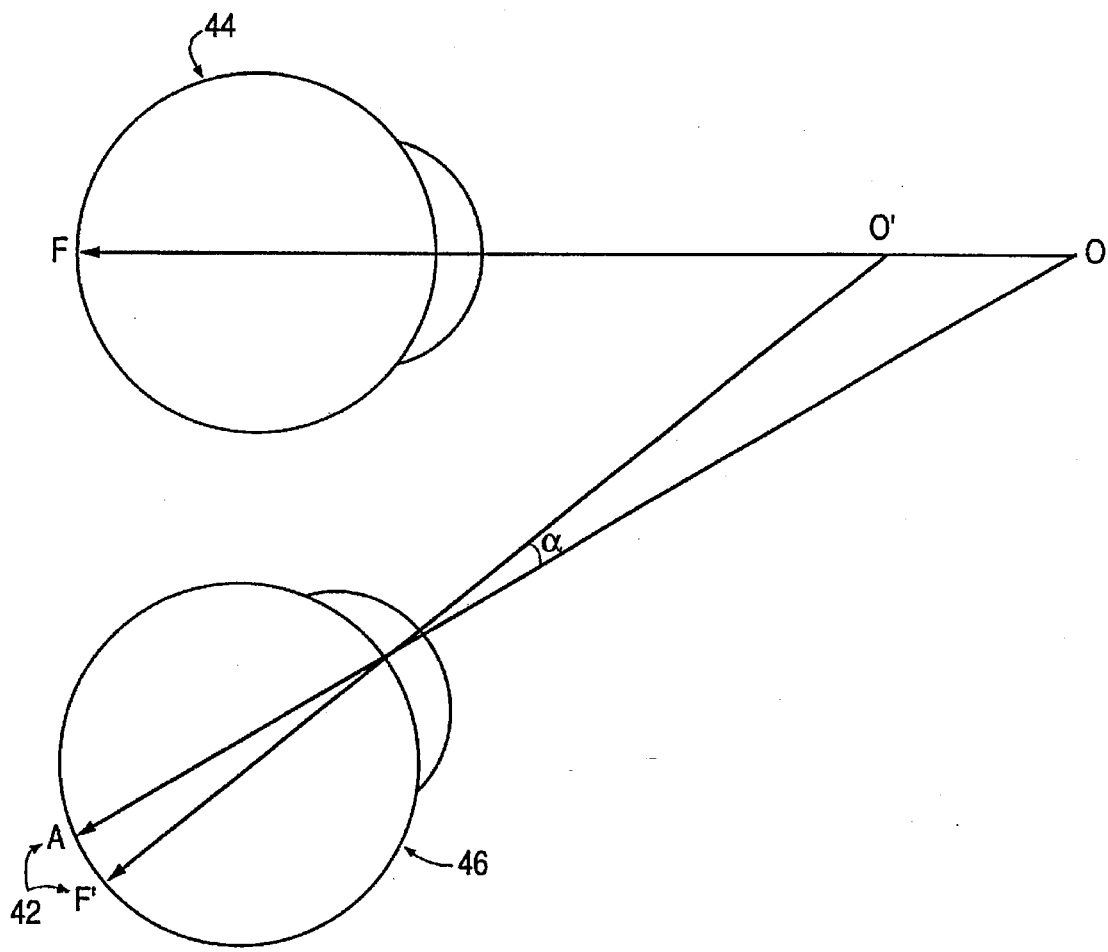
FIG. 4A. Shows the non-alignment of optical axis in a patient with strabismus looking at a near object.
Figure 4B:
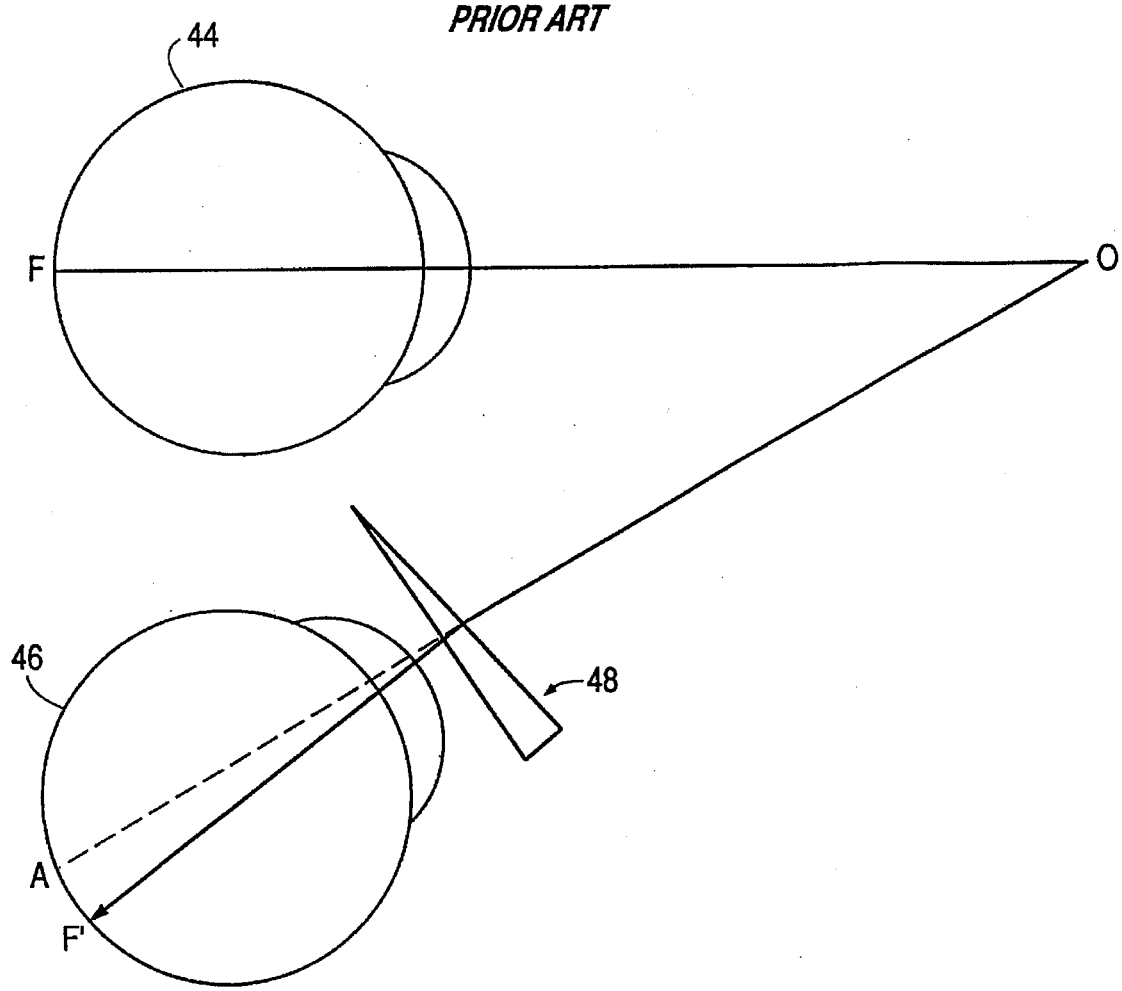
FIG. 4B. Shows the prior art method to correct diplopia.
Figure 4C:
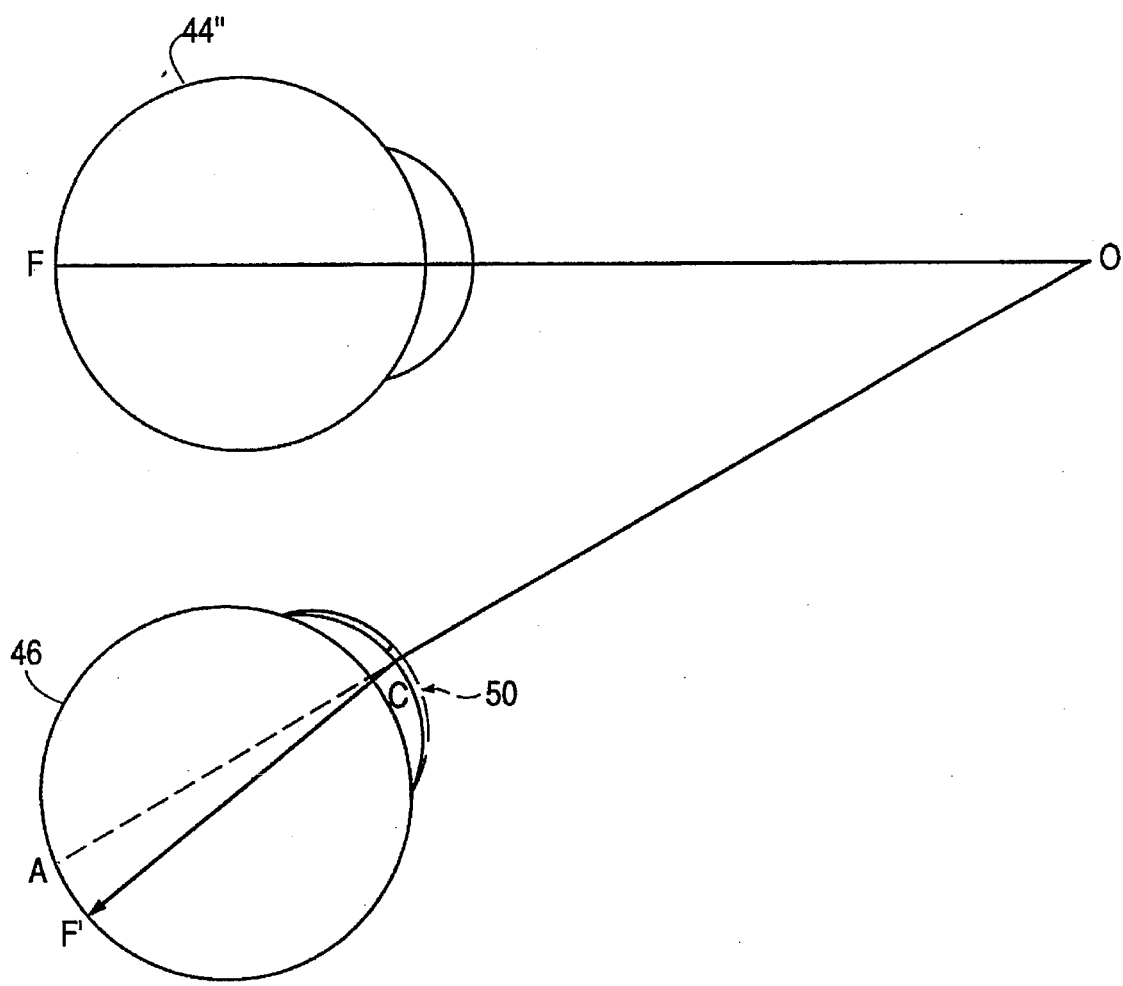
FIG. 4C. Shows the present invention use of prismatic cornea ablation to correct diplopia.

FIGS. 4A, 4B and 4C show the non-alignment of optical axes in patients with strabismus. In FIG. 4A the patient is looking at a near object and because of non-alignment of optical axis will see a double image of object O. In the nondeviated eye depicted above 44, the image of O falls on the fovea F. In the deviated eye 46, the image of object O falls at point A instead of the fovea $F^1$. The fact that the image falls on foveal (F) and extrafoveal (A) locations in the patient's eyes results in double vision. The angle, $\alpha$, between the double images 42 is known as the angle of deviation. In the undeviated eye 44 the object is focused on point F on the retina; however, for the deviated eye 46, the image falls on extra fovea location (A) giving the patient the impression of seeing two objects (diplopia). FIG. 4B shows the prior art method to correct diplopia. A prism lens 48 is placed in front of the deviated eye 46 so that rays from the object (O) going to extra fovea location (A) are deviated by prism 48 and focus on the correct foveal location (F'). FIG. 4C shows the invented use of prismatic cornea ablation to correct diplopia. A cornea prism 50 is produced by tissue ablation in the deviated eye 46 in accordance with the present invention. Light rays from the object (O) hitting the cornea prism lens 50 are deviated toward the correct fovea location (F'), thus correcting diplopia. Particular techniques used to sculpture the prism lens in the cornea are taught in the following specific embodiments; however, the scope of this invention contemplates other methods of corneal ablations including prismatic cornea ablation not specifically disclosed.

Figure 5:
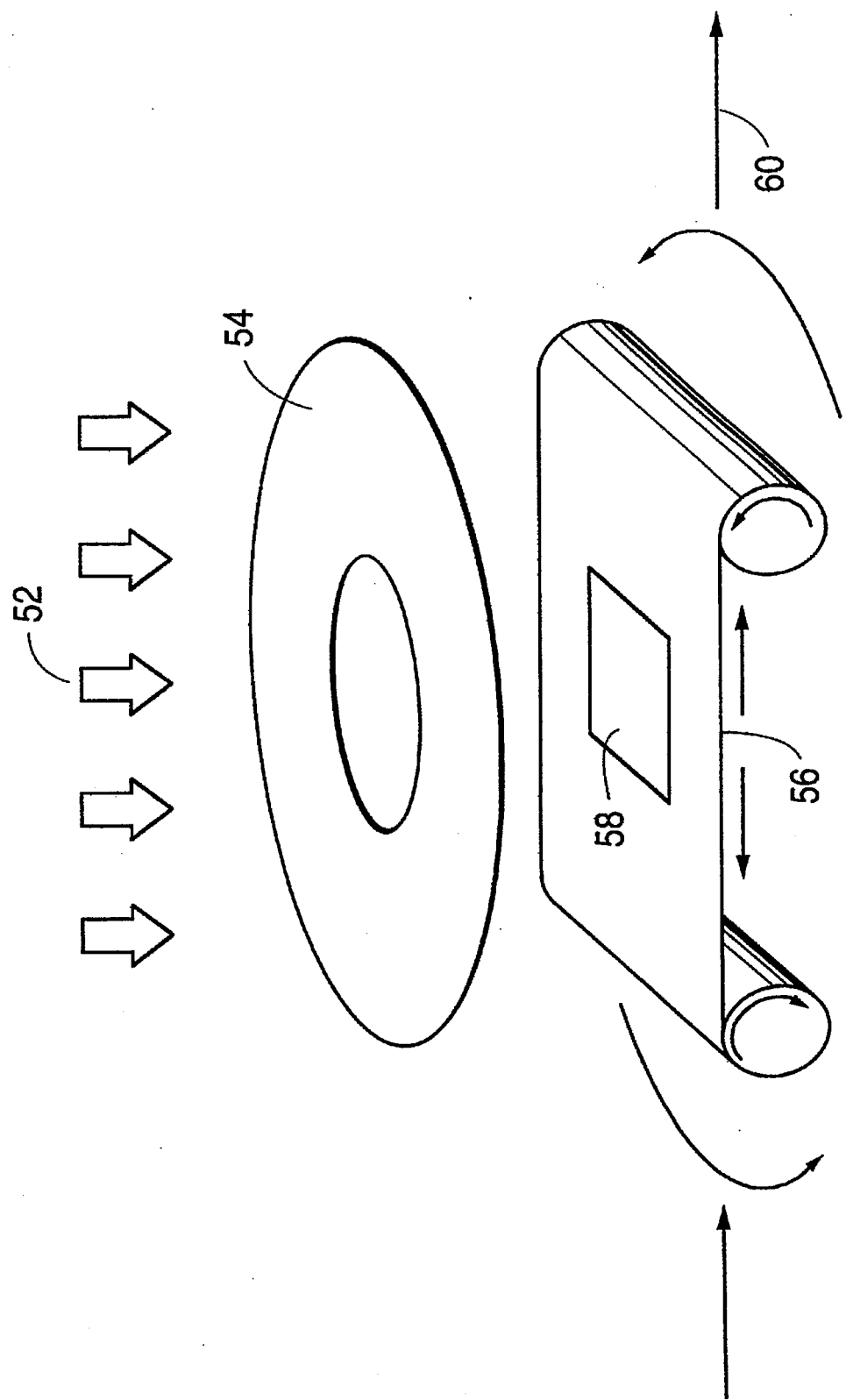
FIG. 5. A generalized embodiment of the apparatus to perform the truncation method of prismatic corneal ablation.

The first embodiment of the present invention taught by FIGS. 5 and 6 is called the truncation method of prismatic corneal ablation. In this technique, a single prism is sculptured into the optical zone of the cornea. FIG. 5 shows a representative embodiment of an apparatus to perform truncated prismatic cornea ablation. A laser source, preferably an excimer laser, produces a light beam 52 that impinges on opaque diaphragm 54. A hole in diaphragm 54 passes a portion of the light beam essentially equal to the intended optical zone (generally 6 mm). A movable opaque shutter containing an opening 58 is scanned across the light beam in a unidirectional manner along the axis of treatment 60. The resulting modulated light beam hits the patient's eye and accurately sculpts a truncated prism on the cornea. The axis of treatment 60 can be varied and the scan rate of shutter 56 is adjustable. The "opaque" diaphragm and shutter may be made of transparent material that is "opaque" to the specific laser wavelength used. The openings in the diaphragm and shutter will then transmit the laser beam, but the surrounding (which is transparent to visual light wavelengths) does not.

As shown more particularly in FIGS. 6A and 6B the shutter speed will effect the depth of ablation and thus the degree of prismatic correction. In FIG. 6A repeated passes of the shutter at a predetermined scan velocity, v, allow light beam 52 to form a series of continuous images shown graphically at 62. The light beam modulated in this embodiment will ablate the cornea as shown at 64. At time "0" there is no prismatic ablation, at time 1 prism GAQ 01 is ablated, at time 2 prism HBP02 is ablated, at time 3 prism ICN 03 is ablated, at time 5 prism KEC 05 is ablated and when the shutter cycle is completed at time 6 prism F06 is ablated. With faster shutter speed, as shown in FIG. 6B (i.e. greater velocity $v^1$), the depth of ablation and the degree of prismatic correction are reduced.

The process of prismatic ablation may be repeated as often as necessary to achieve greater degrees of prismatic correction. The preferred embodiment is that of repeated ablations at higher shutter speeds in order to reduce surface discontinuities that may result from laser beam inhomogeneities, and from eye movement of the patient during the procedure.

This first embodiment is most useful in cases where minimal prismatic correction is required. For larger prismatic correction the truncation method may result in sculpture cuts which abate a significant portion of the anterior stroma; this can cause undesirable scarring. The truncation method cuts a prism into the Bowman's layer which may dip into the underlying cellular anterior stroma layer (which is more acceptable). However, for a large optical zone or for larger diopter changes significant ablation of the cellular layers in the anterior stroma may result. FIG. 7 shows the same prismatic effect cut into the cornea except for different size optical zones ($OZ_1$, $OZ_2$, and $OZ_3$). Angles 1, 2 and 3 are equal resulting in three equivalent prismatic corrections. The greater the optical zone requires greater depth of ablation. As is also readily understood from FIG. 7, the greater the angle 1, 2 and 3, the greater the prismatic effect and the greater the depth of ablation.

Figure 8A:
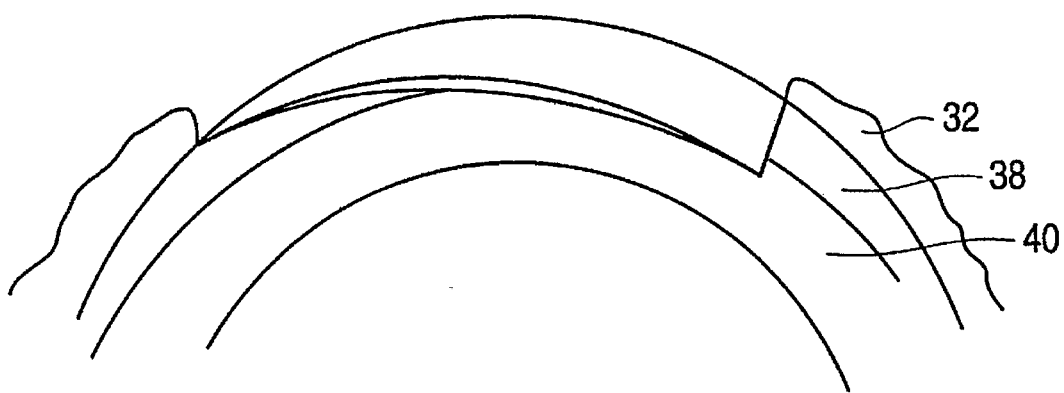
FIG. 8A. The truncation method result for comparison to the Fresnel method of FIG. 8B.
Figure 8B:
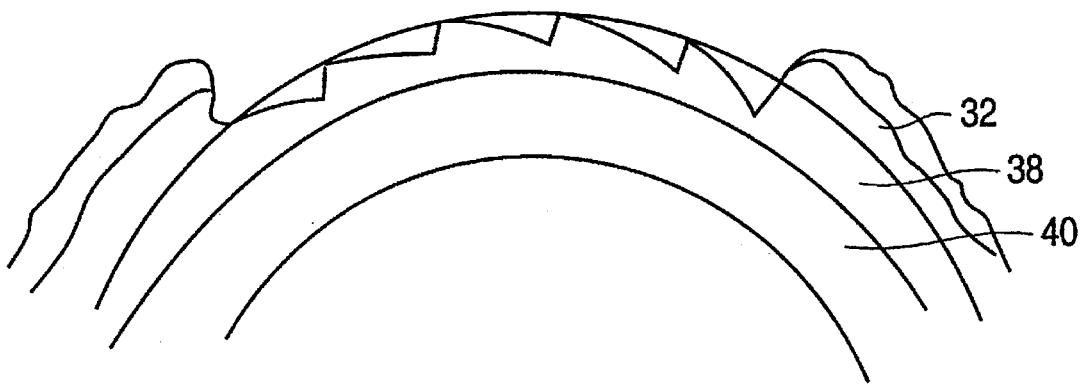
FIG. 8B. The Fresnel prismatic ablation result for comparison to the truncation method result of FIG. 8A.

The second embodiment, shown in FIG. 8B, utilizes Fresnel prismatic ablation to effect a larger diopter change with less depth of penetration into the cornea. FIG. 8A shows the truncation prismatic embodiment to be used for comparison with the Fresnel prismatic embodiment shown in FIG. 8B. In FIG. 8A a single truncated prism having the same radius of curvature as the untreated surface is sculptured into the cornea. Because of the larger diopter change needed for this portion, the ablation penetrates past the Bowman's layer 38 into stroma 40. In FIG. 8B, a plurality of shallower Fresnel prisms are sculptured into the cornea. The same prismatic result is obtained in the Fresnel prism embodiment and the ablation will substantially remain within Bowman's layer 38.

Figure 9A:
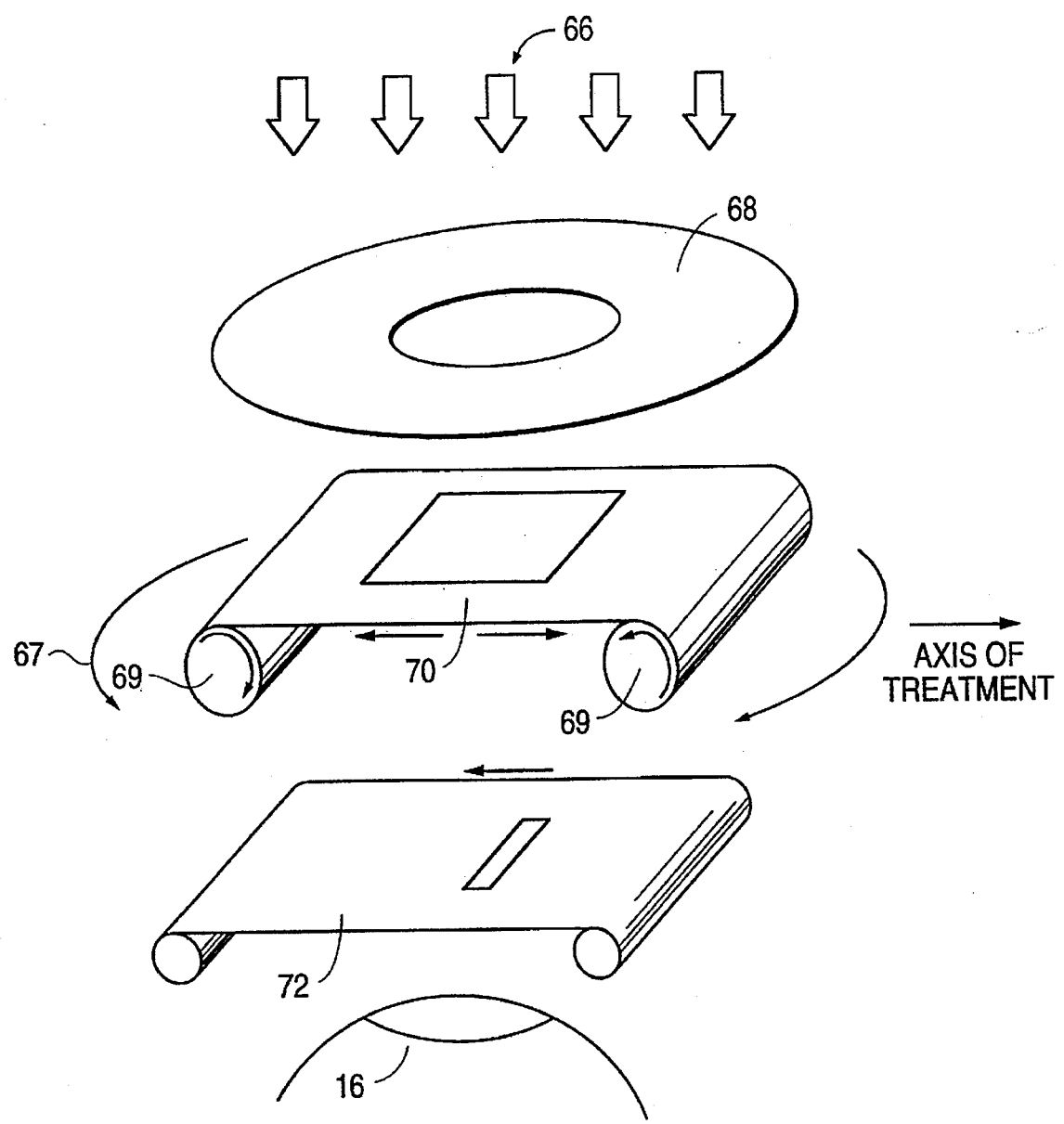
FIG. 9A. A generalized embodiment of the apparatus to produce the Fresnel prismatic corneal ablation.
Figure 9B:
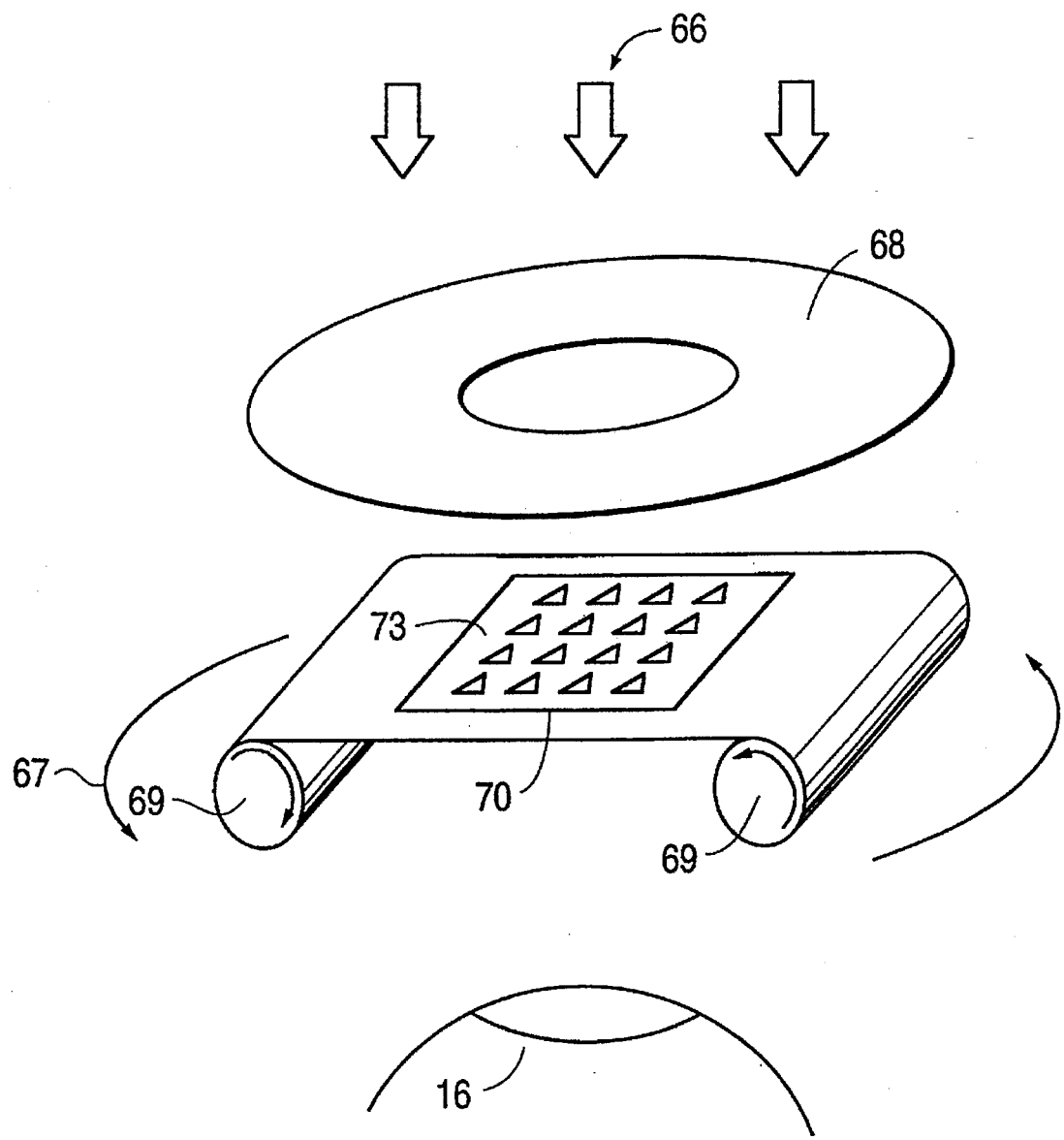
FIG. 9B. Another embodiment to produce Fresnel prismatic ablation.

A generalized embodiment of the apparatus necessary to produce Fresnel prismatic corneal ablation is shown in FIGS. 9A and 9B. A light beam 66, generated by an appropriate laser, is impinges opaque diaphragm 68. The center hole in diaphragm 68 is sized so that the resulting optical beam approximates the desired optical zone of the patient. The resulting beam is then modulated by two shutter 70, 72. First shutter 70 has a center opening which is scanned along a selected axis of treatment across the optical beam. The axis of treatment can be varied by a rotating platform 67 and the speed for shutter to cross the beam is also adjustable by engines 69. The second shutter 72 contains a smaller opening which is moved in a pulsed manner synchronized with, and along the same axis as, movement of shutter 70. The second shutter 72 is pulsed at a time when the first shutter 70 has scanned a distance equal to the width of the second shutter aperture. The second shutter 72 is pulsed to a position such that the opening in the second shutter is now adjacent to the position of the opening prior to the pulse. The net result is that the beam is modulated by the diaphragm and shutters to cut the Fresnel shaped prisms into the cornea 16. The relative speed of shutter 70 will determine the diopter power of the resulting prism; the slower the scan the greater the prismatic diopter change. The relative number of pulsed positions in the shutter 72 will determine the number of Fresnel cuts. If a large diopter change is desired, to minimize the ablation to the anterior stroma, more Fresnel cuts would be programmed by the shorter more frequent pulsed positions of shutter 72.

FIG. 9B shows another embodiment using a preset diopteric correction plate 71 that is placed in the opening of shutter 70. The second shutter 72 is not utilized. By laterally moving the triangular openings 73 in the preset plate, a Fresnel prism is shaped into the cornea 16.

Figure 10A:
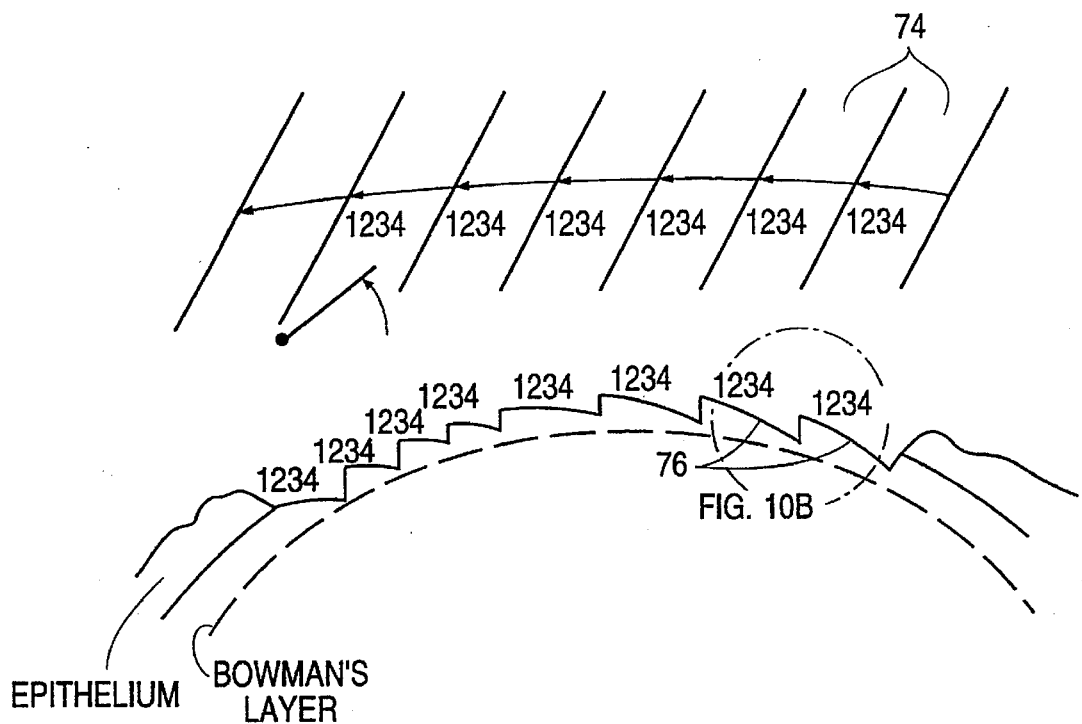
FIG. 10A. Shows the Fresnel prisms cut into the cornea by the apparatus of FIGS. 9A and 9B.
Figure 10B:
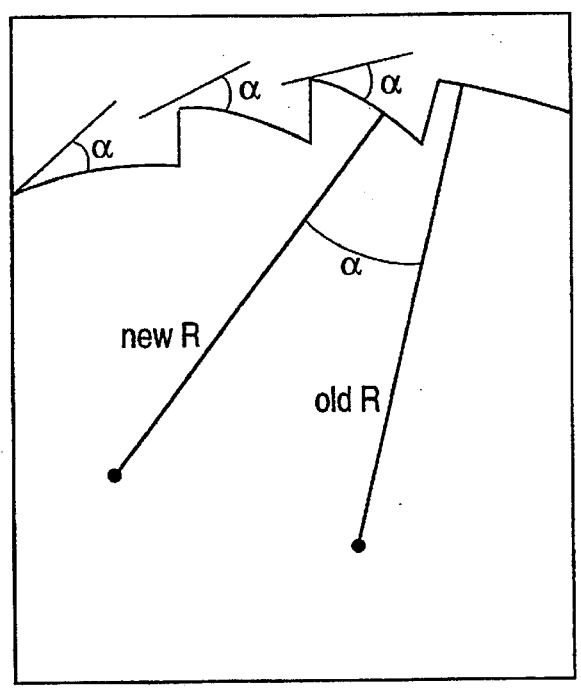
FIG. 10B. Shows the angle between the new surface and a tangent to the old surface to be constant for each cut.

FIG. 10A shows the Fresnel prisms cut into the cornea by the apparatus of FIGS. 9A and 9B. As the second shutter 72 produces progressive slits as shown as elements 74, the first shutter 70 scans across the slit generating prism cuts shown generally as elements 76. The Fresnel prisms are cut so that the angle between the new surface and a tangent to the old surface is kept constant (see FIG. 10B). Keeping this angle constant assures the same radius of curvature as in the untreated cornea surface thus not changing refraction. If refraction correction in addition to prismatic correction is desired this angle can be increased or decreased to effect the deserved refractors change.

It is to be understood that the embodiment shown in FIGS. 5 and 9 are for illustration only. The mechanical diaphragm and shutter(s) could be replaced by liquid crystal or other electronically controlled element to achieve the same effect. A laser beam can alternatively be scanned over the corneal surface to produce differential ablation and subsequent reshaping of the cornea into Fresnel or non Fresnel prismatic pattern. In FIG. 5 the apparatus contains a means for progressively opening a shutter along a linear axis. In FIG. 9, the apparatus contains a means for introducing progressively slits and progressively opened a shutter for each slit along a linear axis.

Figure 11A:
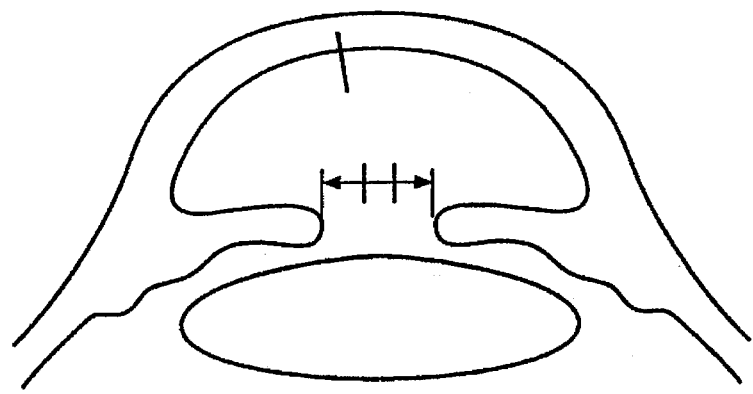
FIG. 11A. Shows the cornea prior to decentration.
Figure 11B:
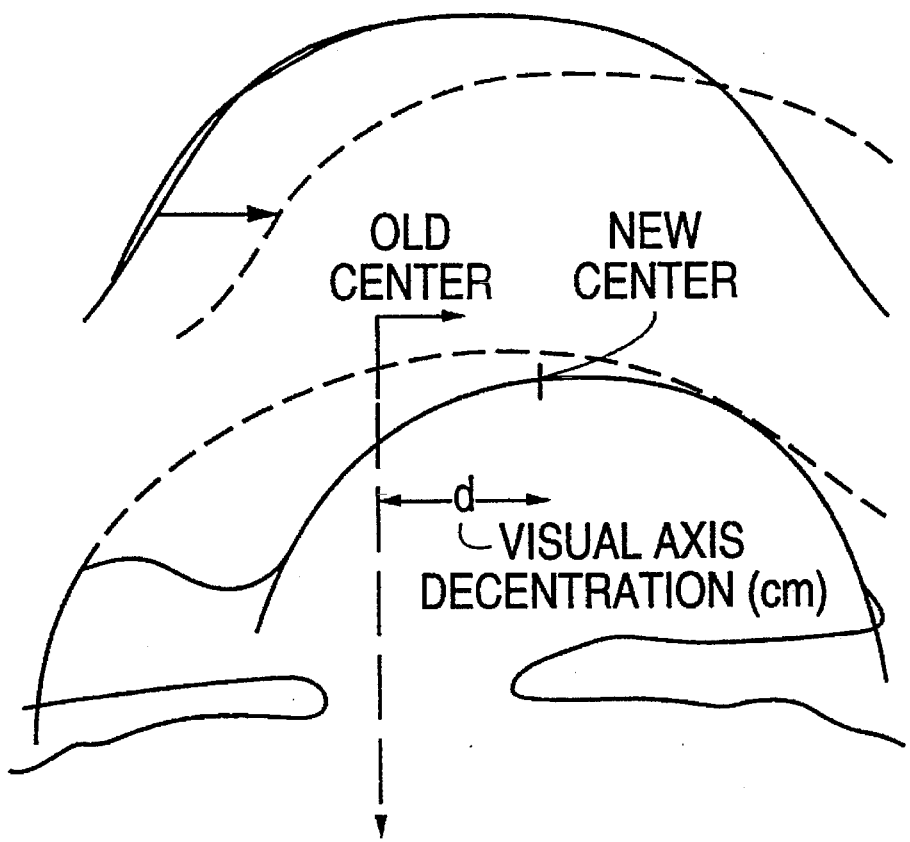
FIG. 11B. Shows the cornea after it has been reshaped resulting in a moved optical center.
Figure 12:
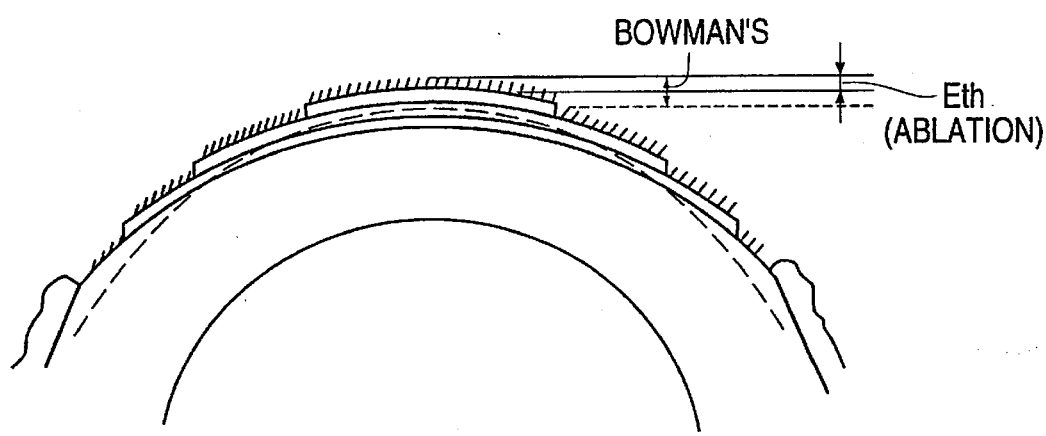
FIG. 12. Shows a Fresnel lens cut in the Bowman's layer.
Figure 13:
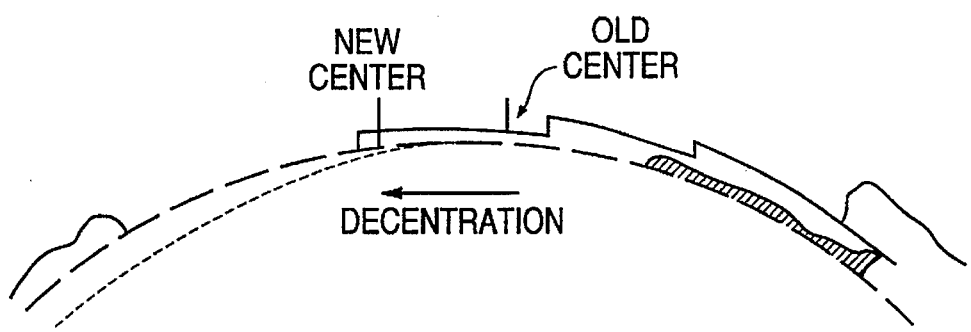
FIG. 13. Shows the decentration embodiment.

A third embodiment of the present invention called decentration is shown in FIGS. 11–13. In FIG. 11, the cornea is reshaped by moving the optical center. Movement of the optical center has a prismatic effect described by Prentice's Rule. According to Prentice's Rule, shown below, a change in visual axis decentration (in era) has a direct prismatic effect (in diopters):

Prism (PD)–Diopters (~45D)•visual axis decentration (cm)

As shown in FIG. 11A, when the optical center is located at the apex of the cornea center there is no prismatic effect. However, if the cornea is reshaped, as shown in FIG. 11B, so that the optical center is moved a distance (d) a prismatic effect results. It will be noted that in FIG. 11B the new radius of curvature is still equal to the old radius of curvature so that no refractive change has been made.

FIG. 13 shows the decentration embodiment in which the prismatic effect is generated by sculpturing a series of Fresnel lenses (not prisms) into the cornea that have a different optical center from that of the cornea prior to treatment. FIG. 12 shows a Fresnel lens cut in the Bowman's layer. Each concentric ring is ablated into the controlling the laser to generate a series of concentric bands. Each band is sculptured with the some radius of curator; however, if the radius of curvature is adjusted to be different from the original untreated radius of curvature refractive changes can be made. As shown in FIG. 13, if the center of the concentric band is moved from the untreated optical center a prism effect is produced. This prism effect is also governed by Prentice's Rule so that the induced prism effect is equal to 48 times the decentration in cm. Therefore, if 2 mm of decentration is sculptured in the cornea, the result will be a prism effect of 20 prism diopters. Thus by utilizing decentration and Fresnel steps, significant prismatic corrections can be achieved without cornea scarring (by staying within Bowman's layer) and using concentric ring diaphragms or similar apparatus to achieve the concentric band effect.

Figure 14A:
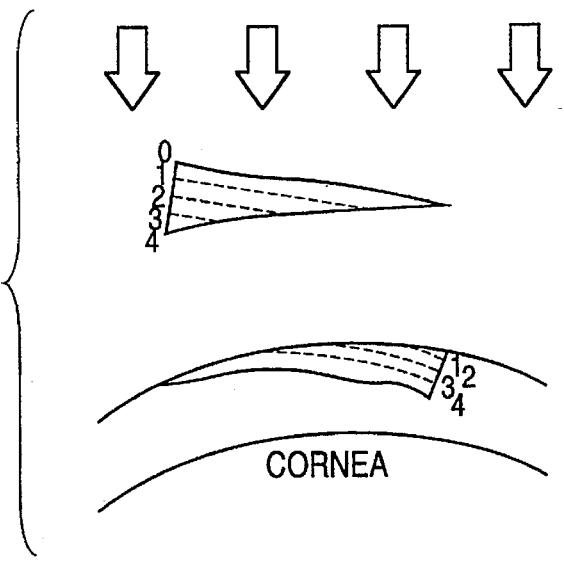
FIG. 14A. Shows the embodiment of an ablatable prism resulting in prismatic corneal ablation and the relationship of the prism to the amount of photoablation.
Figure 14B:
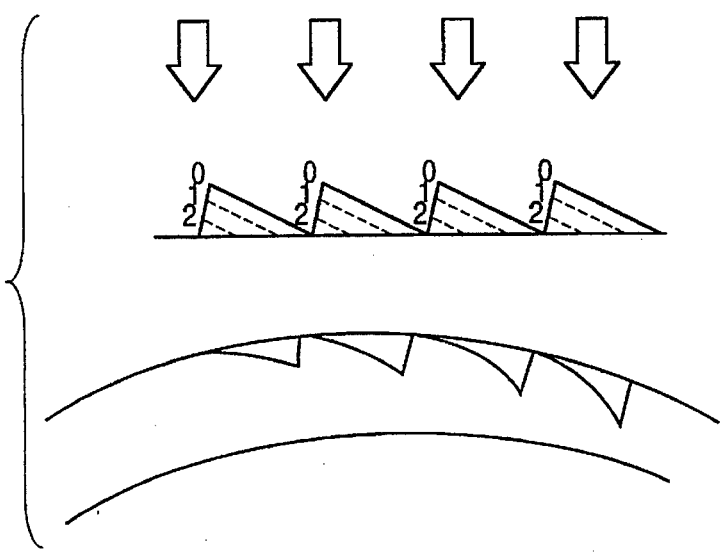
FIG. 14B. Shows the embodiment of an ablatable Fresnel prism resulting in Fresnel prismatic corneal ablation.

An ablatable prism may be alternatively used to produce a prismatic ablation of the cornea, whether Fresnel (FIG. 14B) or non Fresnel (FIG. 14A) in configuration. The ablatable prism may have similar or different ablation rate (and index of refraction) from the cornea. The area of the cornea under the thickest part of the prism receives the least amount of photoablation, and the area of the cornea under the thinnest part of the prism receives the greatest amount of photoablation (FIG. 14). If refractive correction is required in addition to the prismatic correction (which is usually the case in many patients with pediatric strabismus) then the ablatable prism may have a myopic refractive element that will result in intended correction (FIGS. 15 A & B). This ablatable prism can have a hyperopic element (FIG. 15C and 15D) ablatable prism.

FIG. 15A shows the cross section of a minus lens ablatable element that can correct myopia. By truncating such a lens (FIG. 15B), the laser ablation of the new lens will achieve correction of diplopia (or strabismus) as well as myopia.

FIG. 15C shows the cross section of a plus lens ablatable element that can correct hyperopia. Prismatic truncation of such a lens will result in an ablatable element (FIG. 15D) that will correct diplopia (or strabismus) as well as hyperopia. Obviously, similar prismatic truncation can be utilized in conjunction with spherocylindrical ablatable lenses in order to correct combined astigmatism and diplopia.

Obviously, many modification and variations of the present invention are possible in light of the above teachings. It is therefore to be understood that within the scope of the appended claims the inventions may be practiced otherwise than as specifically described.

What is claimed is:

1. In an eye of a patient afflicted by strabismus wherein said eye is made of a cornea comprising an epithelium layer, a Bowman's layer below said epithelial layer, and a stroma below said Bowman's layer operating to focus light from an optical center of said eye about a visual axis to an undesired foveal location, a method for correcting the strabismus by steps comprising:

moving the optical center of said eye by changing the shape of said cornea to move the optical center of said eye away from the visual axis to a desired foveal location and correct the strabismus.

2. In an eye of a patient afflicted by strabismus in which light is deviated from desired focus on a desired foveal location within said eye, wherein said eye has a cornea comprising an epithelium layer, a Bowman's layer below said epithelial layer, and a stroma below said Bowman's layer, a method for correcting the strabismus by steps comprising:

forming a prismatic correction into the Bowman's layer, the stroma, or both the Bowman's layer and the stroma of said eye by photo ablation with a laser, said prism exhibiting a shape sufficient to deviate the focus of light to the desired foveal location and correct the strabismus.

3. A method according to claim 2 wherein the forming step comprises:

forming a fresnel prism into the Bowman's layer, the stroma, or both the Bowman's layer and the stroma.

4. A method according to claim 2 wherein the forming step comprises:

forming a plurality of prismatic corrections into the Bowman's layer, the stroma, or both the Bowman's layer and the stroma.

5. A method according to claim 2 wherein the forming step comprises:

passing a laser light beam through an opening in a shutter moving unidirectionally at a velocity predetermined to form said prism in tissue of the cornea at depths sufficient to correct the strabismus.

6. A method according to claim 2 wherein the forming step further comprises:

forming said prismatic correction in a strabismus-correcting shape and a correction factor of 1–10 prism diopters.

7. A method according to claim 2 wherein the forming step further comprises:

forming said prismatic correction in a strabismus-correcting shape without changing refractive focal length of said eye.

8. A method according to claim 2 wherein the forming step further comprises:

forming said prismatic correction in a strabismus-correcting and a myopia-correcting shape.

9. A method according to claim 2 wherein the forming step further comprises:

forming said prismatic correction in a strabismus-correcting and a hyperopia-correcting shape.

10. A method according to claim 2 wherein the forming step further comprises:

forming said prismatic correction in a strabismus-correcting and an astigmatism-correcting shape.

11. In an eye of a patient afflicted by strabismus wherein said eye is made of a cornea comprising an epithelium layer, a Bowman's layer below said epithelial layer, and a stroma below said Bowman's layer, and said eye focuses light from an optical center of said eye about a visual axis to an undesired foveal location, a method for correcting the strabismus by steps comprising:

moving the optical center of said eye by forming a series of fresnel lenses into the Bowman's layer of said cornea, wherein said fresnel lenses have a different optical center from the optical center of said cornea before treatment and direct focused light to a desired foveal location.

* * * * *